United States Patent [19]

Calabrese et al.

[11] Patent Number: 5,409,901
[45] Date of Patent: Apr. 25, 1995

[54] THERAPEUTIC COMPOSITIONS COMPRISING NUCLEOPROTEINS AS THE ACTIVE AGENTS, AND METHODS OF PRODUCING AND USING SUCH COMPOSITIONS

[76] Inventors: Alberto I. Calabrese, 7292 Av. del Libertador, 10th Fl. "A", 1429 Buenos Aires; Santiago I. E. Calabrese, 1961 Olazabal St. PB, 1428 Buenos Aires; Juan Nakasone, 384 Nother St., 1846 Adrogue, Province of Buenos Aires, all of Argentina

[21] Appl. No.: 442,489

[22] Filed: Nov. 27, 1989

Related U.S. Application Data

[63] Continuation-in-part of Ser. No. 213,403, Jun. 30, 1988, abandoned.

[30] Foreign Application Priority Data

Jul. 2, 1987 [AR] Argentina ................. 308044

[51] Int. Cl.6 ............................................. A61K 37/10
[52] U.S. Cl. .................................... 514/21; 530/358
[58] Field of Search ................. 514/21, 824; 530/358, 530/852

[56] References Cited

U.S. PATENT DOCUMENTS

| | | | |
|---|---|---|---|
| 2,089,227 | 8/1937 | Ruskin | 530/358 |
| 3,322,629 | 5/1967 | Dyke | 514/21 |
| 3,681,283 | 8/1972 | Yueh | 530/358 |
| 4,701,442 | 10/1987 | Revici | 514/21 |

Primary Examiner—Merrell C. Cashion, Jr.
Assistant Examiner—Choon Koh
Attorney, Agent, or Firm—Fleit, Jacobson, Cohn, Price, Holman & Stern

[57] ABSTRACT

The present invention relates to the production of nucleoproteins, more especially DNA, and their use in therapeutic compositions suitable for the treatment of neoplasms, pathological conditions, infections, osteoarticular disorders and the like, which comprise said nucleoproteins as active agent.

Similarly, the invention comprises compositions which protect against the harmful effects of radiation and poisons in general, which also comprise said nucleoproteins as active agent.

Finally, the present invention relates to a method for treating patients suffering from neoplasms and the like, whereby therapeutically effective quantities of said compositions are administered to the patient.

1 Claim, No Drawings

THERAPEUTIC COMPOSITIONS COMPRISING NUCLEOPROTEINS AS THE ACTIVE AGENTS, AND METHODS OF PRODUCING AND USING SUCH COMPOSITIONS

This application is a continuation-in-part of application Ser. No. 07/213,403, filed Jun. 30, 1988, now abandoned.

FIELD OF THE INVENTION

The present invention relates to the production and use of nucleoproteins originating from lysed cells of various kinds, such as nucleated red cells and animal gametes (especially sperm of bull, ram and fish semen) or yeast or pollen cells, which are applicable for the formulation of pharmaceutical compositions that are useful as an analgesic and for the treatment of diseases of diverse etiology, such as infectious diseases (bacterial, viral, and the like), osteoarticular disorders (arthritis, rheumatism, and the like) and neoplasms (in their different cytohistopathological variants). More especially, the invention relates to the production and use of DNA, compositions which include the latter and their use in the treatment of particular diseases. Said compositions have proved useful as anabolic agents, as immunomodulators (of cellular or humoral natural immunity) and also in the protection against the harmful effects of radiation and poisons in general. The study is carried out and the results achieved enable the usefulness of nucleoproteins in retarding cell ageing, and as active agent or factor in tissue regeneration and in bone calcification, to be observed.

As stated above, it also relates to the application of the nucleoproteins of said origin for the treatment of the abovementioned conditions and disorders, by administering therapeutically effective and pharmacologically acceptable quantities, in formulations which include them as active agent, carried in suitable excipients according to traditional pharmaceutical forms (pessaries, suppositories, injectable preparations, ointments, etc.).

DESCRIPTION OF THE PRIOR ART

Biological treatments of cancer were the subject of hypothesis and experimental attempts which date from the beginning of this century and even earlier. The hope of having methods which might destroy the host's cancer cells, via sera prepared against cancer cells injected into animals, motivated the work of Jensen (1903), who injected mouse cancer cells into rabbits, subsequently obtaining a serum which decreased the size of mouse tumors, or caused small implanted tumors to resorb, but in an inconsistent manner. Gaylord, Clowes and Beslock in 1905 obtained, from the blood of mice in which spontaneous resorption of tumors had been produced, a serum having a retarding effect on the development of transplanted cancers of mice.

Erlish in 1906 performed implantations of tumors of low activity in mice, said implantation being repeated periodically with more active tumors until the situation was obtained where the thus immunized could resorb the most virulent tumors in a proportion of 50 % to 80 % of the implanted mice.

These attempts at increasing the animal's immunity on grafting experimental cancers were repeated by Bashford in 1906, without the need to graft tumor cells, but simply using blood of healthy mice.

A study of far-reaching importance was that of G. Schone, who in 1906 achieved an increase in the immunity of mice by grafting normal mouse embryos.

To these promising immunological attempts were added many others, which now remain forgotten since these experimental successes were repeated only in an attenuated form in human tumors.

Bacterial cells, such as that of the erysipelas streptococcus and of other microorganisms, were also used in the desire to increase cancer immunity, but some partial successes were countered by permanent negative results which caused said attempts to be abandoned.

Therapeutic efforts based on "orchitic" medication were published in P. Menetrier's work, page 654, from which we obtain this historical background (6), by Brown-Sequard and D'Arsonval, quoted by Lambert in his thesis on the treatment of cancer in 1901, good palliative results being obtained on human tumors, which results were not confirmed according to Menetrier. Isch-Wall in 1896 also published the use of "testicular fluid" with apparently good results, similar to those obtained by Brown-Sequard.

DETAILED DESCRIPTION OF THE INVENTION

The use of nucleoproteins according to the present invention is based on studies in experimental medicine and in clinical investigation with isolated nucleoproteins, both of bull, pig and lamb epididymis and of fish or of nucleated avian red cells and also of yeasts and pollen, of diverse origins, in the treatment of diseases, namely vascular diseases (arteriosclerosis and arterial hypertension) and neoplastic diseases (experimental in laboratory rats, and in human beings), with the following results:

1. The treatment produces focal and general reactions.
2. Spermatotherapy produces local improvement: reduction in the tumor size.
3. The treatment produces general improvement: disappearance of pains, reappearance of the appetite, and the like.
4. A shock of the protein and/or allergic type may appear.
5. There is very good survival.

The present invention is based on the discovery that certain properties of nucleoproteins which are manifested with the experimental and clinical application of the latter are explicable according to the following hypotheses.

1. Genetic Hypothesis:

It may be considered that the male gametes used, irrespective of their origin, namely human, animal or plant, possess a principle which directs normal cellular multiplication, capable of inhibiting the anarcic development of cancer cells.

As a possible confirmation of this assumption, it may be deemed appropriate to recall here the words of Karl Baner in his lecture on mutation and cancer: tumor cells are genetically identical but different from their parent cells. Cancer cells are always variants of the normal cell. For carcinogenesis, the mutation of the somatic cells has the following interpretation:

A) Once cancerization has occurred, it is transferred without any modification to the daughter cell.

B) The daughter cells of cancer cells will always be cancer cells and never normal.

C) This process is irreversible even when the cause of the cancerization has ceased to act, etc.

It is considered that certain biological components might cause reversion of said mutation, or at least change the type of the daughter cells originating from cancer cells, and this biological component might be none other than the gamete cells.

That is to say, nucleoproteins (DNA or deoxyribonucleic acid) would have an effect of reorienting the generic mutation of neoplastic cells. The nucleus of the sperm cell (male gamete) would thus have a capacity to direct multiplication of normal tissues, applicable also to cancer cells, capable of inhibiting the anarchic multiplication of neoplastic cells.

2. Antigenic Hypothesis:

The nucleoproteins used are administered in sterile form; these compounds generate antibodies when injected, and it is possible to accept the view that the body, being capable of producing substances which lyse the injected cells, which are similar in their capacity for multiplication to cancer cells, may act not only against the gametes used, but also against the selfsame cancer cells.

Study of the "in vitro" effect on nucleoproteins on human lymphocytes demonstrated a significant increase the number of active E. total E, and EA rosette-forming cells. The lymphocytes were characterized and appear to represent the immature T lymphocyte population. It was demonstrated that they are present in a significantly low number in patients bearing solid tumors, and might be an early expression of a relapse. This decrease also correlates with an increase in the suppressor activity of the peripheral lymphocytes.

The fact that nucleoproteins (DNA) are an effective stimulator of killer (NK) cells (with antibody-dependent cytotoxic activity), which are characterized by possessing specific receptors for the Fc fragment of IgG on their membrane, and, on the other hand, that double-stranded RNA molecules or poly(I) or poly(C)[18] and probably DNA are to be found among inducers of interferon synthesis (interferon being a natural substance produced by various types of cells, with an important role in the maintenance of the immnological equilibrium), suggests that the observed effect obtained with the nucleoproteins (DNA) of the gamete or yeast cell might correspond to two types of mechanisms or to the combination thereof:

A) Via a direct action of the nucleoproteins (DNA) on the immunocompetent cells.

B) Via the formation of interferon, which acts by modulating the expression of the surface antigens of the cells, especially those of histocompatibility, and of the receptors for IgG Fc. By either mechanism, the nucleoproteins (DNA) may be considered to be a new immunorestorative drug, without toxicity and which, through its efficacy, may be of great benefit as an immunoregulatory and immunomodating agent in patients with cancer and acquired immune defficiency syndrome (AIDS).

3. Biochemical Hypothesis:

In this instance, it is postulated that nucleoproteins (DNA) would have (due to their chemical constitution) a trophic quality for cancer cells, which would inhibit their cachectic action on the body, forced to yield to the cancer cells the nutrient components for their constant proliferation, purine bases or nucleoproteins which the cancer cells would be unable to synthesize and which they would take from the surrounding medium, as a result of which the intake of nucleoproteins of sperm and/or yeast cells or of other cell nuclei (nucleated avian red cells) fish, and the like) would explain the improvement in the general state which we observe in treated patients.

In the preparation of the compositions of the present invention, gametes of higher animals, such as bull or ram sperm, obtained according to traditional veterinary techniques and maintaining the appropriate precautions of asepsis and without the application of lubricants, are preferably used on account of their availability and the ease with which they may be obtained. It is also possible to use sperm or seminal fluid obtained by the pulverization of stored epididymis (pig, bovine or ram); it is also possible to use fish ova or sperm, or nucleated chicken red cells.

It is, however, recommended to start with sperm of living animals (obtained "in situ" or stored). This recommendation is unavoidable if account is taken of the relatively low content of sperm cells in the epididymis, the pulverization of which leads to the incorporation of connective tissue cells, which are difficult to absorb. The available sperm is diluted, according to its gamete content, to 10–20 % in hypotonic physiological solution, taking it to a concentration of $1 \times 10^8$ to $2 \times 10^8$ gametes/ml, the solution subsequently being processed by tyndallization, the solution previously being treated with (aqueous) 0.5 % strength phenol and subjected to ultrafiltration.

The compositions of the present invention thus comprise purified nucleoproteins as active agent, in an aqueous vehicle, in the form, for example, of intramuscularly injectable solutions.

Said vehicle is, for example, a physiological solution, preferably hypotonic, with or without glucose. The concentration of nucleoproteins varies according to circumstances (patient's age and state, and the like). Usually, the administration is such as to provide about $20 \times 10^6$ gametes/dose.

Said compositions are prepared according to an "ad hoc" procedure, specific to the present invention, which comprises diluting bovine, ovine or porcine sperm, fish sperm, yeast cells or nucleated red cells with a physiological solution; ultrafiltering the diluted material and then sterilizing it by tyndallization.

The therapeutic treatment of the abovementioned conditions which constitutes another subject of the invention, comprises administering to patients physiologically tolerated quantities of sperm nucleoproteins of the abovementioned diluted in an aqueous vehicle.

STUDIES CARRIED OUT IN ANIMALS WITH CANCER.

Various types of studies were carried out in animals (rats) with various types of cancer.

The trials began in 1952, and have continued to date in patients bearing cancer in various sites. The experiments have been carried out in the Instituto de Medicina Experimental de la Facultad de Medicina (Institute of Experimental Medicine of the Faculty of Medicine) of the University of Buenos Aires (U.B.A.).

39 rats grafted with sarcomas and 22 rats with carcinomas were taken, aged 20 days or more and of various sizes. The results were as follows:

| Series | No. rats | Grth.T. | Tumor S. | Comp. Resp. | Applic. No. |
| --- | --- | --- | --- | --- | --- |

| -continued | | | | |
|---|---|---|---|---|
| Carcinoma | 10 | 24 | 3 × 3 | 7 (70%) | 12 |
| Carcinoma | 12 | 20 | 6 × 6 | 7 (58%) | 14 |
| Sarcoma | 22 | 13 | 6 × 6 | 8 (36%) | 12 |
| Sarcoma | 17 | 16 | 6 × 6 | 12 (70%) | 12 |

| General total: | | | |
|---|---|---|---|
| Series | No. rats | Comp. Resp. | % |
| Carcinomas | 32 | 14 | 63.6 |
| Sarcomas | 39 | 25 | 64.1 |
| | 61 | 39 | 63.9 |

Comments

According to the histopathological results obtained, the following emerges:

Within the tumor, lesions of the involutional type predominate, with inhibition of mitosis, with lesions of the capillaries of the tumor, lesions like those observed the experimentally killed animals due to injection of heterologous sera, I"a lesion all the more interesting for the fact that the animals sacrificed were in very good condition and were feeding normally, demonstrating this phenomenon, according to our impression, that the sperm acts specifically on the tumor and not on the normal tissues, a fact corroborated by the other experiments carried out in animals, in which we have never observed deaths in the 61 experimental rats despite the enormous quantity of nucleoprotein injected and despite the repetition of the injections, thereby demonstrating the lack of toxicity, a fact which we corroborate in clinical observation".

We believe that the experiment on the effect of the nucleoproteins on rat tumors demonstrates the selective effect possessed by the said therapy on tumors and not on healthy tissues, and provides a sound experimental basis for this therapy.

CLINICAL TRIALS

The application of the nucleoproteins was continued in a high number of patients bearing advanced cancer, of various histological types and anatomical sites: Lung, breast, brain, leukemias, kidney, liver, colon, ovary, tonsil, tongue, bladder, esophagus, melanomas, pancreas, bone and soft tissue sarcomas, stomach, uterine cervix, and the like.

Studies of acute, subacute and chronic accumulative toxicity were carried out, no toxic effects which might endanger the patients' life being found; in some cases, phenomena of the allergic type were detected, which yielded to specific treatment (corticoid or antihistaminic), or using the two-stage technique.

The patients accepted for the study are terminal, in a poor general state, having received all conventional treatments (chemotherapy, surgery, radiation treatment, immunotherapy, hormone therapy, and the like).

The therapeutic responses have been very encouraging and the survival rate is high.

Comments

The beginning of the therapeutic response is observed at between 7 and 20 days after beginning the treatment. The average duration of the objective response, namely complete response plus partial response greater than 50 %, has been more than 36 months.

An important fact is that those patients who voluntarily (due to improvement in or disappearance of their cancer and/or metastases) abandoned the treatment develop, after a short time, a progression of their disease, which compels the thought that cancer might be deemed to be a chronic degenerative disease, with episodes in which it becomes acute (endangers the patient's life), that requires non-toxic chronic treatment and monitoring with the passage of time (always).

Another interesting finding is the high 5-year survival rate and the good quality of life.

The patients improve in their general state; it is as if, apart from the antineoplastic effect, the nucleoproteins played an important part in the patient's anabolism.

No phenomena of acute, subacute and chronic accumulative toxicity are observed. There is no drug interaction.

CONCLUSIONS

From the results obtained with the application of nucleoproteins (DNA, deoxyribonucleic acid) in the treatment of advanced cancer and other diseases referred to above, the following conclusions are arrived at:

1. Directing action of the nucleoprotein in the neoplastic cell.
2. Selective tropism of the nucleoprotein for the neoplastic cell, not interfering with normal cells.
3. Non-specific antineoplastic activity in any cyto-/histopathological type of cancer and its metastases.
4. Absence of toxic effects: acute, subacute and/or chronic accumulative.
5. Absence of psycho-organic dependence.
6. No drug interaction is observed. In all patients treated with combination therapy, there was not a single case.
7. There are no contra-indications. The endovenous route is not used; only the intramuscular. Given the possibility of being degraded at intestinal level by endonucleases (in particular, of pancreatic origin), oral administration is not used. The nucleoprotein used topically in combination with vitamin A, in ulceronecrotic lesions of neoplastic and/or vascular origin, with good results.
8. The therapeutic effect appears not to depend on an ideal plasma concentration.
9. It is administered daily, no special technique being required.
10. In some instances, the formation of gluteal abscesses is observed, due to poor technique of administration (poor skin antisepsis).
11. It is administered in two stages, using Besredka's method, subcutaneously, with the object of avoiding drawbacks of protein shock, desensitizing the patient.
12. The initial or prolonged administration generates an undesirable side effect in some patients: characterized by shivering, slight temperature rise (38°-39° C.), sweating, arterial hypotension, weakness, moderate asthenia and, in some cases, anaphylactic type shock, which obliges hospitalization of the patient and special care of the latter. It is consequently expedient to administer an antiallergic beforehand, before the application of the nucleoprotein.
13. It is customary to observe a syndrome of tumor lysis, which is related to dose, frequency of administration and tumor type, characterized by hypercalcemia, hyperuricemia, and the like, which remit with specific treatment.
14. It has a potent analgesic and antirheumatic effect.
15. It is inferred that it has a high capacity for penetration and diffusion to any point in the system in which neoplastic cells are present. It would appear to have a tropism for the tumor cell.

16. The administration of the nucleoprotein is carried out in ambulatory fashion.

17. Focal and general reactions are observed, in the manner of a specific treatment.

18. As regards the local improvement, it is possible to observe deobstruction of the esophagus, and of the testine, reduction in the tumor size and, in some cases, disappearance of the lesion.

19. With reference to the general improvement: reappearance of the appetite, relief of pain, reappearance of muscular strength. In the studies carried out in Wistar rats, a large anabolic effect is observed.

20. We did not observe hemolytic states or coagulopathies due to the use of the nucleoprotein.

21. No adverse electrocardiographic effects or hemodynamic defects were observed.

22. The appearance of a slight pain or of discomfort the metastatic sites and/or in the primary tumor are frequently observed, it being possible for this finding, where appropriate, to be used or exploited as a monitor for lesions or diagnostic tests for concealed metastatic lesions.

23. A stimulatory effect on the natural killer (NK) cells, with antibody-dependent cytotoxic activity, is observed, these cells being characterized by possessing specific receptors for IgC Fc on their membrane, and, on the other hand, it is observed that DNA molecules are to be found among the inducers of interferon synthesis, suggesting that the effect observed after the administration of DNA might correspond to two types of mechanisms or to the combination thereof:

A) via the direct effect of the DNA on the immunocompetent cells.

B) via the formation of interferon, which acts by modulating the expression of the surface antigens of the cells, especially those of histocompatibility, and of the receptors for IgG Fc. This observation has been made "in vitro" and "in vivo".

24. Irrespective of the mechanism, we postulate "DNA constitutes a new non-toxic immunorestorative (immunomodulatory) drug".

25. Following the administration of DNA, we have noted an effect of retarding cell ageing, 50 male Wistar rats being used experimentally the animal house of the Cátedra de Toxicología de la Facultad de Medicina (Department of Toxicology of the Faculty of Medicine) of the University of Buenos Aires (U.B.A.), monitored for approximately 12 months. The evidence for this rests on the following observations:

A) Macroscopic:

Retardation of ageing, the observations being assessed on the basis of the state of liveliness of the animals, state of the joints and trophism of the skin, claws and coats.

B) Microscopic:

The microscopic observations tallied with the macroscopic: maintenance of the normal appearance of the neurons, preservation of the elastic layers of the aorta, enrichment of the cells of the pituitary, preservation of the trabecular structure of the liver and the glycogen reserve, and preservation of the glomerular appearance and of the renal tubules, and of the glandular structures of the prostate and of the testicle, with the presence of a large number of spermatozoa in the latter.

These experimental observations tally with Prof. Alberto Italo Calabrese's clinical experience lasting many years, in the application of this therapy at clinical level (ageing, osteoarthritis, tumors, and the like).

26. A protective effect is observed, not only on the marrow but at multi-organ level, experimentally and clinically, in laboratory rats subjected to radiomimetic substances - 5-fluorouracil - at high doses, followed for several months. It would appear that DNA blocks the toxicity of toxic substances such as radio-active and chemotherapeutic substances.

27. When applied in severe primary mylosclerofibrosis, we found that there was an anarchic mechanism in the hematopoietic organs which was corrected by deoxiribonucleic acid (DNA). When remission of the disease was achieved, there was never any further clinical, laboratory or histopathological evidence betraying activity of the disease.

28. Protective effect on organ transplants, at experimental level following the prior administration of the nucleoprotein (DNA, deoxiribonucleic acid). When anatomopathological studies are carried out in rats in which spleen and ovary were transplanted, the manifest preservation of the implanted tissue is observed, a situation which does not occur in the group of rats which did not receive DNA.

Study on spontaneous tumors

This study was carried out on Wistar rats and Rockland mice. In some of these, the spontaneous development of tumors of the sarcomatous type was established.

Said tumors were treated with DNA (deoxyribonucleic acid) nucleoproteins of bovine gamete cells according to the compositions of the invention, and the inhibitory effect obtained on the tumors is assessed on the basis of micrographs of mouse and rat tumors. It should be emphasized that, during the treatment with the DNA, no signs of toxicity of the latter, nor mortality of the animals through the effect of the exclusive treatment with DNA, were observed.

TABLE No. 1

Experiments carried out in the Instituto de Medicina Experimental (Institute of Experimental Medicine)

| Series | No. of rats treated | Controls | Growth Time | Tumor Size | Therapeutic material | No. of inject. | Completely cured | Proportion | Observations |
|---|---|---|---|---|---|---|---|---|---|
| 9028 carcin. | 10 | 10 | 24 days | 6 × 4 cms | 20% bull sperm 2/10 cc | 12 day on average | 7 | 70% | — |
| 9024 carcin. | 12 | 12 | 20 days | 5 × 3 cms | 20% bull sperm 2/10 cc | 14 day on average | 7 | 58% | 1. tumor involuted to s. slow w/treat. grew |
| 9029 sarcoma | 22 | 8 | 13 days | 6 × 6 cms | 20% bull sperm 2/10 cc | 12 day on average | 8 | 36% | 5. eliminated tumor through ulceration · Not. includ. |

TABLE No. 1-continued

Experiments carried out in the Instituto de Medicina Experimental (Institute of Experimental Medicine)

| Series | No. of rats treated | Controls | Growth Time | Tumor Size | Therapeutic material | No. of inject. | Completely cured | Proportion | Observations |
|---|---|---|---|---|---|---|---|---|---|
| 9060 sarcoma | 17 | 17 | 16 days | 6 × 5 cms | 20% bull sperm 2/10 cc | 11 day on average | 12 | 70% | stud. — |

GENERAL TOTAL:
carcinomas . . . 22 completely cured 14 proportion 63%
sarcomas . . . 39 completely cured 25 proportion 64%
TOTAL: . . . 61 completely cured 39 proportion 63%

ARTERIOSCLEROSIS AND ENGERGIZING ACTIVITY

Through application of nucleoproteins it has been possible to attain the improvement of arteriosclerosis signs and symptoms.

In experimental assays as hereinafter illustrated it was verified that animal senile involution could be successfully stopped, which fact was demonstrated by a biological study carried out during the treatment and through the histological examination of rat viscera, wherein it was appreciated that arterial vessel elasticity as well as kidney, liver, brain, testicle and other viscera structures could be remarkably preserved.

Human beings have showed an improvement of the symptoms of Parkinson shivering, attention, memory, working and sexual ability in old-aged and metabolic improvements such as the lowering of hyperglucemia and of cholesterol levels.

Other symptoms were appetite and anabolysm increase, skin trophism as well as bone and teeth recalcifying.

RAT AGING DELAYING TREATMENT BY THE USE OF GAMMETA CELL

Material and Methods

50 One-year-old male Wistar rats were employed. Twenty-five of them were twice a week injected intramuscularly (i.m.) during approximately 12 months, with the quantity of 20 million bovine spermatozoa. Neither toxic nor allergic reactions were observed. The weight and overall condition of the animals was maintained the persistence of the vital morphological signs of the young adult rat being notorious.

The animals were sacrified and subjected to individual histological examination. Employed techniques were PAS and hematoxylin-eosine, following the conventional method, applied to tissue cuts binded in Bouin and included in paraffin.

The preparations were divided in two groups: those corresponding to the cuts of untreated rats and those to inoculated animals as above mentioned. In both cases the following organs were examined: brain, hypophysis, aorta, liver, kidney, prostate and testicle.

In the brain of untreated animals there can be appreciated a diminution of the neuron size as well as a lower affinity by the dyestuffs employed when dyeing. An increase of the glial elements could be also verified. The arrangement of the neuronal elements seems to be more anarchic and its number reduced.

These particularities cannot be seen in the brain of treated rats where the neuronal size, number, arrangement and tinctorial affinity thereof is higher than in the remaining group; also the amount of glial forms is lower as compared analytically.

The examined hypophysis showed acidophile cells to prevail on basophile and chromophobe cells in untreated cells. Collagen fiber infiltrations as well as mononuclear cells can be likewise seen.

The aorta of untreated rats showed wall structure alterations with the occurrence in control rats of hyaline-fibrous bands in the muscle-elastic layer which are typical of the natural aging process. The outer and inner elastic limits cannot be seen.

Treated animals do not show said hyalinefibrous bands whilst their natural structure remains unaltered. large, connective-type, cells can be found in the different aorta layers.

The liver of untreated rats shows a considerable increase of the trabecular disorganization, cell alteration signs (absence of mitosis forms) and a remarkable diminution of the PAS tinctorial affinity (indirect sign of the diminution of the glycogenic storage).

There phenomena do not occur in treated rats or else they are restricted to diminute liver tissue zones. No mononuclear infiltrates can be either seen in Kiernan spaces.

Control rat, kidneys verify a marked retraction with a tendency to the hyalinization of glomerules and a moderate disorganization of tubular components (especially in the skirted close tube; loss of the brush-type border).

In treated rats glomerular alterations are smaller; the tubules as well as the membranous microdowns show a better preserved structure.

The prostate of untreated animals present both a bigger disorganization in the epithelial portion and a smaller tinctorial affinity, whilst the glandular structure and colour riches of treated rats appear to be better preserved.

The testicles of untreated rats present tubular alterations such as changes in the cytologic distribution with diminution both of the spermatozoa number and spermatogenesis, together with a slight to moderate vacuolization of the Sertoli cells. The intertubular space shows a diminution of Leydig cells along with structural and tinctorial affinity modifications thereof.

In treated rats the alterations are not so notorious, the majority of the tubules showing an almost normal appearance, and the number of spermatozoa being markedly higher. The intertubular space features are identical to those of young a adult rat.

The results of this experimental assay are believed to be promising. Its uses have already been clinically applied for years, its favourable palliative effect on tumours and arthrosis, old age arteriosclerosis and physical consequences thereof, as well as on intoxications by cythostatics and radiations having been reported by the literature. Its application is deemed to be easy, innocuous and not very onerous, and in view of the noted results its benefits are intended to be extended to vast sectors of the community.

SUMMARY

One year old Wistar rats have been used in the experiment, treated with bovine gene cells i.m. every second day, over a period of about months, with an amount of 15 million spermatozoa per injection.

Marked macroscopic evidences of the senescence retardation were obtained. It could be evaluated by the animals' state and vivacity: articular state and skin, nails and hair trophism. The macroscopic evidences were confirmed by the microscopic findings; neurons maintained their normal aspect; the aortic elastic layer was conserved; pituitary gland cellularity increased; the liver conserved its trabecular structure and glycogen storage; kidneys conserved their glomerular aspect and tubules; and there was a conservation of the glandular structure in prostate and testicles with the presence of abundant spermatozoides within the latter.

The experimental observations confirmed the clinical experiences of the author in the use of this therapy, in many years of clinical duties, in the treatment of neoplastic diseases, senescence, arthrosis, as well as intoxication by radiations, citostatic drugs and another poisons, etc.

ENERGIZING ACTIVITY IN NUCLEOPROTEIN-TREATED RATS

The effects on rats were examined as follows. The animals walked up to exhaustion at a given speed on a treadmill.

A 800A electrified grill acted as aggressive stimulus. The animals were afterwards distributed in two groups (one of them as a control group). Three hours later the test was repeated, and the significance of the observed differences was statistically verified (the length of time required for the exhaustion of the animals was measured before and after the treatment).

In the exhaustive swimming test, two groups of rats were made to carry weights equivalent to the tenth part of their body weight and swim till they plunged due to exhaustion. One of the groups was injected with nucleoproteins whilst the remaining one was kept as a control group.

Three hours later the test was repeated and it was observed that control animals plunged earlier than in the first test, whilst animals treated with nucleoprotein injections showed an identical performance and in many cases even surpassed it in a statistically significant manner.

RHEUMATISM

The assays were carried out on rats suffering from articular alterations induced with tuberculous toxin, which upon local inflammatory reactions produces a generalized arthrosis.

The simultaneous administration of nucleoproteins counteracts arthrosis due to its diminishing and corrective effect on articular inflammation provoked by the tuberculous toxin.

Upon administration of the nucleoprotein treatment to human beings, in 90 percent of the cases rheumatic pain disappeared whilst articular mobility and working ability improved. In comparison therewith, administration of placebos attenuated pain in only 10 percent of the cases, whilst no improvement was observed in the articular mobility or working ability of the patients.

The following examples illustrate the employed techniques and obtained results:

TREATMENT OF ARTHROSIS WITH GAMETIC CELLS NUCLEOPROTEINS

The proved usefulness of the deoxyribonucleic acid derived from gametic cells and its further components in the treatment of osteoarticular degenerative and inflammatory processes led the applicants to study its effectiveness of arthrosis disease.

At this end there were selected 40 patients suffering in one hip from 2- and 3- stage arthrosis, as clinically and radiologically certified.

The 40 patients were asked to fulfill over two months the following requirements:

1) to take adequate doses of exclusively clinical medicines;
2) medicines should not be changed over the entire period;
3) not to be attended by any rehabilitating therapy; and
4) the process must be stationary.

The object of the research was to determine efficacy and safety (secondary actions) parameters.

Efficacy parameters
Function
Pain
Walking
Vicious attitude
Safety parameters
Pulse
Blood pressure
Weight
Percussion
Liver palpation
Toxic effects
Laboratory tests

| Evaluation of the hip (in accordance with the method of Iowa University) | |
|---|---|
| A. Function (35 points) | |
| 1) He does the greatest part of his work or household chores requiring mobilization | 5 |
| 2) He dresses with no help (including shoes tying or putting stockings on) | 5 |
| 3) He walks enough to keep his independence | 5 |
| 4) He sits (at table or toilet) with no difficulty | 4 |
| 5) He picks up objects from the floor by crouching | 3 |
| 6) He bathes with no help | 3 |
| 7) He masters the stairs one foot after each other | 3 |
| 8) He masters the stairs in any manner | 2 |
| 9) He carries objects similar to a briefcase | 2 |
| 10) He gets on cars or public transport with no help and he travels comfortably | 2 |
| 11) He drives a car | 1 |
| B. Pain (35 points) | |
| 1) Absence of pain | 35 |
| 2) Pain appears only when getting tired | 30 |
| 3) Pain appears when carrying heavy objects | 20 |
| 4) Pain appears when being at rest but not when carrying heavy objects | 15 |
| 5) Pain appears when sitting or laying | 10 |
| 6) Continuous pain | 0 |
| C. Walking (10 points) | |
| 1) With no shirking, with no support | 10 |
| 2) With no shirking, with stick | 8 |
| 3) Shirking under abduction | 8 |
| 4) Shirking due to shortened member | 8 |
| 5) Two sticks are required | 6 |
| 6) Two crutches are required | 1 |

| Evaluation of the hip (in accordance with the method of Iowa University) | |
|---|---|
| 7) He cannot walk | 0 |
| D. Absence of vicious attitude (10 pts.) | |
| 1) No vicious attitude | 10 |
| 2) Fixed flexion greater than 30° | 3 |
| 3) Fixed abduction greater than 10° | 3 |
| 4) Fixed rotation greater than 10° | 2 |
| 5) More than 1 cm shortening | 3 |

Urine:

pH
proteins
glucose
sediment

Method

The test population was divided into 2 groups of 20 patients each.

The first group was exclusively administered over 60 consecutive days a daily i.m. ampoule of DNA suspension derived from gametic cells.

The control group was administered placebo at identical doses and frequency.

The results of previous examination of the 20 patients, based on the Iowa University method were as follows:

| No. of Patients | Score |
|---|---|
| Function* | |
| 3 | 28 |
| 6 | 23 |
| 7 | 19 |
| 4 | 18 |
| *normal score: 35 | |
| Pain* | |
| 2 | 30 |
| 5 | 20 |
| 9 | 15 |
| 4 | 10 |
| *normal score: 35 | |
| Walking* | |
| 20 | 8 |
| *normal score: 10 | |
| Vicious Attitude* | |
| 14 | 3 |
| 6 | 2 |
| *normal score: 10 | |

Upon expiration of the research period, patients having been drug-administered were subjected to re-examination and the results were as follows:

| No. of Patients | Score |
|---|---|
| Efficacy parameters: | |
| Function | |
| 6 | 32 |
| 8 | 27 |
| 5 | 24 |
| 1 | 21 |
| Pain | |
| 5 | 33 |
| 6 | 27 |
| 5 | 20 |
| 4 | 16 |
| Walking | |
| 5 | 10 |
| 15 | 8 |

| No. of Patients | Score |
|---|---|
| Vicious Attitude | |
| 8 | 8 |
| 6 | 7 |
| 6 | 6 |

Safety parameters

The following side effects were observed:
1. Two patients had a two and three day fever, respectively, which eased up with ordinary antipyretics and which did not force the suppression of the medicines.
2. One patient suffered from a two-day urticaria rash. He rapidly improved upon antihistamine administration. The therapy was not suppressed.
3. Local pain at the injection site in one patient, which was spontaneously over the day after.

Two cases with local pain upon injection were reported in the control group.

| | Analysis of the results | |
|---|---|---|
| | % Improvement upon admin. with | |
| Parameter | Drug | Placebo |
| Function | 100* | 10 |
| Pain | 100* | 25 |
| Walking | 75 | 0 |

*at different stages

Insignificant side effects which did not affect the administration of the treatment were reported in 4 drug-treated cases and 2 placebo-treated cases, respectively.

Conclusions

The results obtained in the treatment of arthrosis with nucleoproteins and further components of the gametic cell demonstrate the high therapeutical efficacy and absence of toxicity of the drug.

The superiority of the efficacy parameters was extraordinarily significant as compared with the control group.

AIDS

In laboratory proofs it was observed that the in vitro addition of nucleoproteins to the blood of patients suffering from AIDS stimulated both the formation of small roses in lymphocytes T4 and the production of NK (natural killers) cells.

Symptoms such as adenopathies, fever, sweat, loss of weight, anorexy, diarrhoea, bronchitis, hepatitis, etc. in AIDS patients disappeared thanks to the periodical and repeated treatment with nucleoproteins.

The periodical administration of nucleoprotein injections in AIDS patients showing no apparent manifestation of the disease maintained the good general condition and absence of symptoms, even when the patients were undergoing stressing situations such as drug addiction, excessive efforts, insufficient diet, etc.

The employed technique and obtained results were as follows:

Nineteen patients bearing AIDS and showing clinical manifestations of the disease, such as loss of weight, fever, multiple adenopathies, hepatosplenomegaly, bronchitis, etc. were thrice a week administered i.m. nucleoprotein injections.

Seventeen patients gained between 1,500 and 9,500 kg. Only two patients lost 1 and 3 kg., respectively, which results in a 89.46 percent improvement average.

INTOXICATION DUE TO RADIATIONS AND RADIOMIMETIC DRUGS

There has been observed that Wistar rats as well as mice were more tolerant and that their mortality diminished when radiated and simultaneously protected with nucleoprotein injections. Similarly, when rats were intoxicated with radiomimetic drugs there was observed a higher preservation and greater number of spinal cord elements such as white and red globules and platelets.

In human beings said tolerance can be verified through the absence of symptoms and signs of intoxication by X-rays and radiomimetic drugs such as nausea, vomiting, anemia, leukopenia, etc. This diminution of toxic effects upon administration of nucleoprotein injections permitted the use of radiations and radiomimetic drugs in the treatment of cancer at doses greater than the conventional ones, thus yielding better results than those obtained without the use of nucleoprotein injections.

The following Tables show the normality of the hematic condition of a patient suffering from lung cancer over 30 consecutive days with 5FU by venous route and nucleoproteins by intramuscular rote.

It can be appreciated that the hematologic condition is normal in spite of that duration and frequency of administration being increased.

| Date | Red blood cells | Leucocytes | Neutrophiles | Eosinophiles | Lymphocytes | Monocytes | Platelets | Erythrocytes | |
|---|---|---|---|---|---|---|---|---|---|
| 7-X-67 | 3,800 | 8,000 | 67 | 5 | 24 | 4 | — | 100 | Case P.E.C. |
| 18-X-67 | 3,750 | 6,500 | 67 | 2 | 30 | 1 | — | 100 | |
| 31-X-67 | 3,100 | 6,400 | 64 | 2 | 32 | 4 | 160 | 90 | |
| 8-XI-67 | 3,000 | 6,000 | 66 | 1 | 30 | 3 | 180 | 100 | |
| 16-XI-67 | 3,400 | 6,500 | 71 | 1 | 24 | 2 | — | 80 | |
| 29-XI-67 | 3,600 | 8,000 | 77 | 3 | 19 | 1 | 200 | 110 | |

HEMATIC CONDITION OF PATENTS TREATED WITH RADIOMIMETIC DRUGS & PROTECTED WITH NUCLEOPROTEINS

| CASES/AGE | TYPE OF LESION | TREATMENT | APPETITE BEFORE NUCLEOPROTEINS | APPETITE AFTER NUCLEOPROTEINS | PAIN BEFORE NUCLEOPROTEINS | PAIN AFTER NUCLEOPROTEINS |
|---|---|---|---|---|---|---|
| C1 ♀ 60 | SIGMOID CANCER | 5 FU CICLOFOSFAMIDE | (−) | (+) | (+++) | (+) |
| C2 ♀ 41 | BILATERAL BREAST CANCER | ADRIAMICIN 5 FU//METROTEXATE CICLOFOSFAMINE | (− −) | (+) | (++++) | (−) |
| C3 ♂ 38 | HODGKINS | PROCARBAZIDE CICLOFOSFAMIDE VINCRISTIDE | (+) | (+++) | (−) | (−) |
| C4 ♀ 49 | BREAST CANCER | HEDERINE | (−) | (+++) | (++) | (−) |
| C5 ♂ 65 | LIVER CANCER | 5 FU CICLOFOSTAMIDE METOTREXATE | (− − −) | (−) | (++) | (−) |
| C6 ♂ 53 | LUNG CANCER | VINBLASTIN THIO-TEPA | (− − −) | (+) | (++) | (−) |
| C7 ♀ 45 | BREAST CANCER | ADRIAMICIN 5FU METOTREXATE CICLOFOSFAMIDE | (−) | (++) | (−) | (−) |
| C8 ♀ 59 | BREAST CANCER | ADRIAMICIN 5 FU METOTREXATE CICLOFOSFAMIDE | (− −) | (++) | (+) | (−) |
| C9 ♀ 42 | PANCREAS CANCER | 5 FU CICLOFOSFAMIDE METOTREXATE | (− − − −) | (−) | (+) | (−) |
| C-10 ♀ 32 | HODGKINS | PROCARBAZIDE CICLOFOSFAMIDE VINCRISTIN | (+) | (++) | (−) | (−) |

| CASES/AGE | TYPE OF LESION | TREATMENT | RED CORPUSCLES BEFORE | RED CORPUSCLES AFTER | COLORLESS CORPUSCLES BEFORE | COLORLESS CORPUSCLES AFTER | PLATELETS BEFORE | PLATELETS AFTER |
|---|---|---|---|---|---|---|---|---|
| C1 ♀ 60 | SIGMOID CANCER | 5 FU CICLOFOSFAMIDE | 3 m. | 3.8 m. | 3.000 | 5.000 | 150.000 | 500.000 |
| C2 ♀ 41 | BILATERAL BREAST CANCER | ADRIAMICIN 5 FU//METROTEXATE CICLOFOSFAMINE | 2 m. | 4.2 m. | 800 | 6.000 | 80.000 | 250.000 |
| C3 ♂ 38 | HODGKINS | PROCARBAZIDE CICLOFOSFAMIDE VINCRISTIDE | 3.05 m. | 4.5 m. | 1.200 | 5.000 | 160.000 | 300.000 |
| C4 ♀ 49 | BREAST CANCER | HEDERINE | 3 m. | 4.43 m. | 6.800 | 7.000 | 180.000 | 290.000 |

HEMATIC CONDITION OF PATENTS TREATED WITH RADIOMIMETIC DRUGS & PROTECTED WITH NUCLEOPROTEINS -continued

| | | | | | | | | | |
|---|---|---|---|---|---|---|---|---|---|
| C5 65 | ♂ | LIVER CANCER | 5 FU CICLOFOSTAMIDE METOTREXATE | 2.9 m. | 4.1 m. | 2.500 | 6.200 | 120.000 | 230.000 |
| C6 53 | ♂ | LUNG CANCER | VINBLASTIN THIO-TEPA | 3.5 m. | 4.25 m. | 4.000 | 6.400 | 130.000 | 250.000 |
| C7 45 | ♀ | BREAST CANCER | ADRIAMICIN 5FU METOTREXATE CICLOFOSFAMIDE | 2.9 m. | 3.9 m. | 4.200 | 5.800 | 110.000 | 220.000 |
| C8 59 | ♀ | BREAST CANCER | ADRIAMICIN 5 FU METOTREXATE CICLOFOSFAMIDE | 3.1 m. | 4.2 m. | 3.000 | 6.300 | 130.000 | 260.000 |
| C9 42 | ♀ | PANCREAS CANCER | 5 FU CICLOFOSFAMIDE METOTREXATE | 2.8 m. | 5.9 m. | 4.500 | 5.800 | 140.000 | 190.000 |
| C-10 32 | ♀ | HODGKINS | PROCARBAZIDE CICLOFOSFAMIDE VINCRISTIN | 2.5 m. | 4 m. | 8.200 | 6.000 | 125.000 | 210.000 |

ORGAN TRANSPLANTATION

Rat spleen transplantations were successfully carried out to rats by protecting the transplanted organ with nucleoprotein injections before and after the implant operation.

One month later, the biopsy proved the preservation of the spleen tissue whilst the spleen of untreated animals was destroyed by the immunologic rejection.

The method was repeated but transplanting rat ovaries. In those animals protected with nucleoprotein injections the ovary continued to be normal and produced nature ovules, whilst control animals showed that the ovary had been almost totally reabsorbed.

Consequently, nucleoprotein injections are indicated for preventing the rejection of transplanted organs both in animals and human beings.

The following experimental results support what has been previously stated.

AND DERIVED FROM GAMETIC CELLS AS PROTECTING AGENT OF RAT OVARY TRANSPLANTATION

Material and Method

Female Wistar rats weighing 200–250 g each were employed. The sexual cycles were controlled by respective vaginal washing and microscopic control.

There was employed general ethereal anesthesia under glass bells and once the desired place was reached, the animal was fixed with a contention support. In all cases there was effected a dorsolumbosacrum incision to release the ovary from its anatomical position, there being effected a liven-thread binding in its vasculonervous package.

The removed organ was re-implanted in the receiving animal which 15 days earlier had been subjected to ovary ectomization in the right iliac fossa with a pexy to parietal peritoneum, one plane muscle suture, skin suture with agraphia.

In order to prevent chirurgical sepsis the animals were injected p.o. over 3 days with 50,000 IU sodium penicillin each 12 hours. Feeding and water were libitum.

The transplanted animals are divided in two groups: control and test group. The latter receive gametic cells derived from bull sperma at a concentration of 100,000 spermatozoa per cubic meter.

The diluent is physiological serum in 5/000 phenol and sterilized by successive tyndalization. From this suspension 0.5 ml were daily injected i.m. over 20 days starting from the day they received the donor ovary.

Once said period of time had elapsed, the animals were sacrified and subjected to necropsy.

The ovaries were macroscopically observed in both groups.

EXAMPLE 1

Preparation of DNA from "lysed gametes".
1) Gametes originating from mammals are obtained and stored in phenol at a concentration of 0.5 % (five parts per thousand)
2) The material is centrifuged and washed to remove the phenol.
3) The gametes are subjected to cell lysis through the action of dilute trichloroacetic acid at pH 2, and the action of heat until the DNA is broken into nucleotide portions.
4) The material is subjected to a control chromatographic run to stop the hydrolysis at this level.
5) The acidity is neutralized by means of a suitable buffer to obtain a pH of 7.
6) The material is lyophilized.
7) The material is packaged in ampoule vials containing 100 or 200 milligrams of dry substance, according to the conditions for which the drug is intended.

EXAMPLE 2

Specific composition for pharmaceutical use.
1) A preservative [mercury ethylthiosalicylate at a concentration of 1/10,000 (one part per ten thousand)]added to the DNA material.
2) The material is sterilized by means of a "tyndallization at 75° C. for 2 hours, this operation being repeated every 24 hours for 3 consecutive days.
3) The sterile material obtained is lyophilized in an aseptic medium in ampoule vials which contain 100 to 200 milligrams, according to the conditions to be treated: for example, 100 milligrams in arteriosclerosis or rheumatism and 200 milligrams in cases of cancer.
4) In separate ampoules, a diluent for the DNA, based on 10 mg of phenylhydramine and 1% of xylocaine, introduced: 2 cc or ml in total.

EXAMPLE 3

1) Obtaining semen
a) Hygienic preparation of the male. Washing of the genitals and of the skin of the inguinal regions in order to remove bacterial dust, plant debris, and the like. Sterilization of the artifical vagina. It is not lubricated with liquid paraffin because the latter would become incorporated with the seminal fluid and is difficult to remove, and because it causes pain.
b) Preparation of the preserving fluid Phenol is used at a concentration of 0.5 % (five parts per thousand), introducing 500 cc into 1 dark-brown flask (sterilized) of capacity 1,000 cc. Sterile distilled water is used as the vehicle.
c) Storage of the semen collected until the flask is filled: stored away from the light. It should not be kept in the refrigerator, in order to facilitate the growth of sporulated microorganisms, which will subsequently be destroyed or attenuated by the phenol.
2) Preparation of the DNA material 1) The phenol is removed by decantation from the sperm
2) The spermatozoa are washed and the volume is returned to its original value
3) The material is filtered through several layers of gauze or other type of filter, to remove undesirable particles (plant matter, earth, and the like)
4) The material is centrifuged
5) The material is suspended in hypotonic (0.4 %) saline solution in a quantity of vehicle for bringing the quantity of spermatozoa to a 10 % strength suspension, that is to say 100 ml of sperm for 900 ml of hypotonic saline solution.

We claim:
1. A method for treating a person suffering from arteriosclerosis, which comprises administering physiologically tolerated and therapeutically effective quantities of a pharmaceutical composition which includes as active agent gamete nucleoproteins of bovine, ovine, porcine or fish sperm, or of yeast cells or of nucleated red cells, suspended in a pharmacologically acceptable aqueous medium.

* * * * *